(12) United States Patent
Shiigi et al.

(10) Patent No.: US 8,404,860 B2
(45) Date of Patent: Mar. 26, 2013

(54) COMPOUND HAVING HYDANTOIN RING AND METHOD OF PRODUCING THE SAME

(75) Inventors: Hirofumi Shiigi, Shunan (JP); Mina Shimamura, Shunan (JP)

(73) Assignee: Tokuyama Corporation, Yamaguchi (JP)

( * ) Notice: Subject to any disclaimer, the term of this patent is extended or adjusted under 35 U.S.C. 154(b) by 0 days.

(21) Appl. No.: 13/556,460

(22) Filed: Jul. 24, 2012

(65) Prior Publication Data

US 2012/0289705 A1    Nov. 15, 2012

Related U.S. Application Data

(62) Division of application No. 12/669,111, filed as application No. PCT/JP2008/062398 on Jul. 9, 2008, now Pat. No. 8,258,313.

(30) Foreign Application Priority Data

Jul. 19, 2007  (JP) ................................. 2007-188157

(51) Int. Cl.
*C07D 487/20* (2006.01)
*C07D 487/10* (2006.01)
*C07D 235/00* (2006.01)

(52) U.S. Cl. .................................................. 548/301.4

(58) Field of Classification Search ................ 548/301.4
See application file for complete search history.

(56) References Cited

U.S. PATENT DOCUMENTS

| 4,952,694 | A | | 8/1990 | Brackeen et al. | |
|---|---|---|---|---|---|
| 5,817,776 | A | * | 10/1998 | Goodman et al. | ............... 534/14 |
| 6,977,267 | B2 | * | 12/2005 | Dhar et al. | ..................... 514/389 |
| 2002/0143141 | A1 | | 10/2002 | Chen et al. | |
| 2004/0077879 | A1 | | 4/2004 | Schafmeister | |
| 2006/0292073 | A1 | | 12/2006 | Goodman et al. | |

FOREIGN PATENT DOCUMENTS

| JP | 2004-123596 A | 4/2004 |
|---|---|---|
| WO | WO 02/18437 A2 | 3/2002 |
| WO | WO 2005/030730 A1 | 4/2005 |

OTHER PUBLICATIONS

Alizadeh, A. et al, "New, diastereoselective one-pot synthesis of tetrasubstituted hydantoins," Helvetica Chimica Acta, 2006, vol. 89, No. 6, pp. 1187-1193.
Chu et al., "Discovery of 1-Amino-4-Phenylcyclohexane-1-Carboxylic Acid and its Influence . . . Pentapeptides", Bioorganic & Medicinal Chemistry Letters, vol. 15, No. 22, pp. 4910-4914, Nov. 15, 2005, XP005098196.
Dörwald, F. Zaragoza. "Side Reactions in Organic Synthesis: A Guide to Successful Synthesis Design," Weinheim: Wiley-VCH Verlag GmbH & Co., KGaA, 2005, Preface.
EPO Communication for Appl. No. 08778007.8 dated Dec. 30, 2011.
Gupta, S. et al, "Synthesis of a Pipecolic Acid-Based Bis-amino Acid and Its Assembly into a Spiro Ladder Oligomer," Organic Letters, 2005, vol. 7, No. 14, pp. 2861-2864.
JPO International Search Report for Appl. No. PCT/JP2008/062398 dated Aug. 5, 2008.
Levins, C.G. et al, "The Synthesis of Curved and Linear Structures from a Minimal Set of Monomers," J. Org. Chem., 2005, vol. 70, pp. 9002-9008.
Levins, C.G. et al, "The Synthesis of Functionalized Nanoscale Molecular Rods of Defined Length," J. Am. Chem. Soc., 2003, vol. 125, pp. 4702-4703.
McConathy, J. et al, "Improved synthesis of anit-[18F]FACBC: improved preparation of labeling precursor and automated radiosynthesis," Applied Radiation and Isotopes, 2003, vol. 58, pp. 657-666.
Mio et al., "Synthesis and Herbicidal Activity of Deoxy Derivatives of (+)-Hydantocidin", Agric. Biol. Chem., vol. 55, No. 4, pp. 1105-1109, 1991, XP002633274.
Niederauer and Glatz, "Advance in Biochemical Engineering," Biotechnology, vol. 47 (1992), pp. 159-161.
Ornstein et al., "2-Substituted (2SR)-2-Amino-2-((1SR,2SR)-2-Carboxycycloprop-1-yl)glycines as Potent and Selective Antagonists . . . Bioavailability", J. Med. Chem., vol. 41, No. 3, pp. 358-378, Jan. 14, 1998, XP002633275.
Vogel, A.I. (Vogel, Arther I.), "Practical Organic Chemistry," Longman Group Limited London, 1956, 3rd Ed., p. 122.
Wrobleski et al., "Cyclobutane Derivatives as Potent NKi Selective Antagonists", Bioorganic & Medicinal Chemistry Letters, vol. 16, No. 14, pp. 3859-3863, Jul. 15, 2006, XP025106293.
Yokum et al. "Synthesis of a Series of of Polar, Orthogonally Protected, α,α-Disubstituted Amino Acids", Tetrahedron Ltters, vol. 38, No. 23, pp. 4013-4016, Jun. 9, 1997, XP004065013.

* cited by examiner

*Primary Examiner* — Yong Chu
*Assistant Examiner* — Valerie Rodriguez-Garcia
(74) *Attorney, Agent, or Firm* — Birch, Stewart, Kolasch & Birch, LLP

(57) ABSTRACT

A method of selectively producing the syn-isomer of a compound having a hydantoin ring, which is important as an optical material, an electronic material, an active ingredient and an intermediate of medicines and pesticides and an active ingredient and an intermediate of diagnostics, comprising converting a compound having a hydantoin ring (for example, (E,Z)-2-benzyloxy-5,7-diazaspiro[3,4]octan-6,8-dione represented by the following formula (1)) into a t-butyl ester derivative thereof (formula (2)), crystallizing the same to selectively give the syn-monoBoc isomer thereof and then leaving the t-butyloxycarbonyl group.

2 Claims, No Drawings

COMPOUND HAVING HYDANTOIN RING AND METHOD OF PRODUCING THE SAME

This application is a Divisional of co-pending U.S. application Ser. No. 12/669,111 filed Jan. 14, 2010, now U. S. Pat. No. 8,258,313, which is the National phase of PCT International Application No. PCT/JP2008/062398 filed on Jul. 9, 2008. This application also claims priority to Patent Application No. 2007-188157 filed in Japan on Jul. 19, 2007. All of the above applications are hereby expressly incorporated by reference into the present application.

TECHNICAL FIELD

The present invention relates to a hydantoin ring compound, which is important for an optical material, an electronic material, an active ingredient or intermediate of medicines and pesticides, and an active ingredient or intermediate for diagnostics, as well as to a method for producing the compound.

BACKGROUND ART

Hydantoin ring compounds are useful as an intermediate for the synthesis of an optical material, an electronic material, an active ingredient or intermediate of medicines and pesticides, or an active ingredient or intermediate of diagnostics.

For production method of a hydantoin ring compound (the compound is hereinafter referred to also as hydantoin derivative), there is known a synthesis method of reacting 3-benzylcyclobutanone with ammonium carbonate, ammonium chloride and potassium cyanide in a water/methanol mixed solvent. In the hydantoin derivative obtained by this method are present a syn-isomer and an anti-isomer, which are both geometrical isomers. Column chromatography has been used for resolution of these geometrical isomers into respective isomers (Non-Patent Literature 1).

Non-Patent Literature 1: Applied Radiation and Isotopes, Vol. 58, p. 657, 2003 2.2 Chemistry

DISCLOSURE OF INVENTION

Technical Problem

When geometrical isomers, optical isomers, etc. are present in medicines used for man and animal, one of the isomers is pharmacologically effective in many cases. When both isomers are present in medicines, the other isomer show serious medicine damage in some cases. In order to avoid this problem, it is necessary to selectively isolate only one isomer functioning as a medicine and use it as a medicine. In this way, the safety and efficacy of medicines are secured.

In the Non-Patent Literature 1, column chromatography is used in order to resolve a pair of geometrical isomers into respective isomers. In the separation of isomers by chromatography, described in the Non-Patent Literature 1, 1 g of a hydantoin derivative is developed in a column filled with 95 g of silica gel to isolate 500 mg of a syn-isomer of the hydantoin derivative.

However, column chromatography is suitable for the small-scale purification of compound and its use in large facility is difficult. Further, column chromatography takes a long time in separation, making low the work efficiency. Furthermore, column chromatography uses a large amount of an eluent, generating a large amount of a waste solution and inviting low economy. Moreover, use of a large amount of silica gel generates a large amount of an industrial waste and the amount of syn-isomer obtained in one operation is extremely small. Therefore, the resolution of geometrical isomers by column chromatography is not a production method usable in industry, from the standpoints of operability, workability and economy.

Hence, it is desired to establish a technique which can use a wide-use facility and which can separate and purify a geometrical isomer or the like by a simple method such as recrystallization, derivation or the like.

Technical Solution

The present inventors made a study in order to solve the above problem. As a result, it was found that, in resolution of isomers of a hydantoin ring compound, efficient reduction in isomer content can be achieved by employing crystallization from a solvent under particular conditions. The present invention has been completed based on the above finding.

Hence, the present invention aims at solving the above problem and providing a high-purity hydantoin ring compound, low in isomer content and a method for producing the compound.

The present invention, which has solved the above problem, is described below.

[1] A method for producing a hydantoin ring compound which is represented by the following formula (I):

[formula 1]

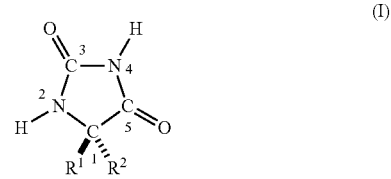

wherein the numerals attached to individual ring-constituting elements represent the positions of the ring-constituting elements; $R^1$ and $R^2$ are different from each other and each an organic group of 1 to 20 carbon atoms, or $R^1$ and $R^2$ bond to each other to form a spiro ring of 3 to 20 carbon atoms bonding to the carbon of position 1; any of $R^1$, $R^2$ and the ring formed by bonding of $R^1$ and $R^2$ contains at least one asymmetric carbon atom, and is low in isomer content by selectively separating one diastereomer of a pair of diastereomers each having a diastereo-face containing the position 1 asymmetric carbon of the formula (I) and one asymmetric carbon present in any of $R^1$, $R^2$ and the ring formed by bonding of $R^1$ and $R^2$, from a mixture of at least one pair of diastereomers represented the formula (I) comprising the pair of diastereomers each having the diastereo-face, the method comprises the following steps of:

(1) reacting, in a solvent, the mixture with at least one kind of protecting agent selected from the group consisting of di-tert-butyl dicarbonate, dimethyl carbonate, diphenyl carbonate, tert-butyloxycarbonyl chloride, tert-butyloxycarbonyl bromide, tert-butyloxycarbonyl fluoride, benzyloxycarbonyl chloride, tert-butyldimethylsilyl chloride, tosyl chloride and benzenesulfonyl chloride, to directly or indirectly form a mixture of at least a pair of "diastereomers each having one protective group" having a structure represented by the following chemical formula (II):

[formula 2]

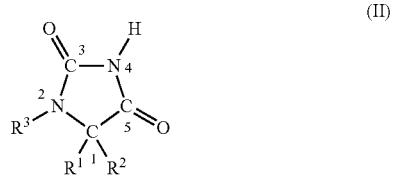

(II)

wherein the numerals attached to individual ring-constituting elements represent the positions of the ring-constituting elements; $R^1$ and $R^2$ have the same definitions as $R^1$ and $R^2$ in the chemical formula (I); $R^3$ is one kind of protective group selected from the group consisting of tert-butyloxycarbonyl group, methoxycarbonyl group, phenoxycarbonyl group, benzyloxycarbonyl group, tert-butyldimethylsilyl group, tosyl group and benzenesulfonyl group,
comprising a pair of "diastereomers each having one protective group" each having a diastereo-face containing the position 1 asymmetric carbon of the above chemical formula (II) and one asymmetric carbon present in any of $R^1$, $R^2$ and the ring formed by bonding of $R^1$ and $R^2$, (2) making one diastereomer of the pair of "diastereomers each having one protective group" selectively precipitated from a solution containing the mixture of at least the pair of "diastereomers each having one protective group" obtained by the reaction during the reaction and/or after the reaction, (3) separating the precipitated diastereomer to obtain a compound of the formula (II) low in isomer content, and (4) contacting the compound of the formula (II) low in isomer content, separated in the above step, with an acid to eliminate the protective group.

[2] In the above method for producing the hydantoin ring compound, the step (1) of forming a mixture comprises following two embodiments. In one embodiment, the step (1) comprises a step of directly forming the mixture containing "diastereomers each having one protective group", and in the other embodiment, the step (1) comprises a step of firstly, forming a mixture of "diastereomers each having two protective groups", represented by the following chemical formula (III)

[formula 3]

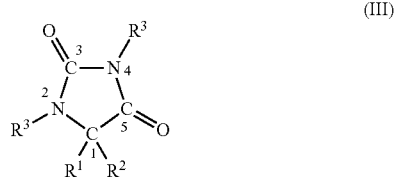

(III)

wherein the numerals attached to individual ring-constituting elements represent the positions of the ring-constituting elements; $R^1$ and $R^2$ have the same definitions as $R^1$ and $R^2$ in the chemical formula (I); $R^3$ has the same definition as $R^3$ in the chemical formula (II),
and then, eliminating the protective group bonding to the position 4 nitrogen atom of each "diastereomer having two protective groups" of the above-obtained mixture, to indirectly form a mixture of "diastereomers each having one protective group".

[3] The selective elimination of the protective group bonding to the position 4 nitrogen atom of each "diastereomer having two protective groups" contained in the above mixture comprises contact of the mixture containing "diastereomers each having two protective groups", with a polar solvent.

[4] Between the step (3) and the step (4), there is conducted a step (3') of purifying the compound represented by the formula (II), low in isomer content, obtained in the step (3).

[5] The purification step (3') of the above [4] comprises wherein the purification step (3') comprises the following steps of:

(3'-1) reacting the compound represented by the formula (II) low in isomer content, obtained in the step (3), with a protective agent to obtain a mixture comprising "a diastereomer having two protective groups" represented by the formula (III), (3'-2) eliminating the protective group bonding to the position 4 nitrogen atom of each "diastereomer having two protective groups" contained in the above mixture to form a mixture containing "diastereomers each having one protective group", and (3'-3) making one "diastereomer having one protective group" of the pair of "diastereomers each having one protective group" selectively precipitated from the mixture solution formed by the reaction in the step (3'-2) during and/or after the reaction.

The present invention is also a hydantoin ring compound represented by the following formula (II):

[formula 4]

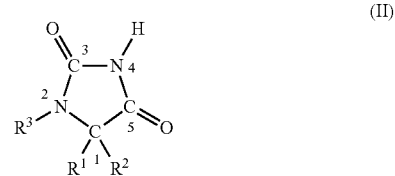

(II)

wherein the numerals attached to individual ring-constituting elements represent the positions of the ring-constituting elements; $R^1$ and $R^2$ are different from each other and each an organic group of 1 to 20 carbon atoms, or $R^1$ and $R^2$ bond to each other to form a spiro ring of 3 to 20 carbon atoms bonding to the carbon of position 1; any of $R^1$, $R^2$ and the ring formed by bonding of $R^1$ and $R^2$ contains at least one asymmetric carbon atom; $R^3$ is one kind of protective group selected from the group consisting of tert-butyloxycarbonyl group, methoxycarbonyl group, phenoxycarbonyl group, benzyloxycarbonyl group, tert-butyldimethylsilyl group, tosyl group and benzenesulfonyl group.

[6] The present invention is further a hydantoin ring compound represented by the following formula (III):

[formula 5]

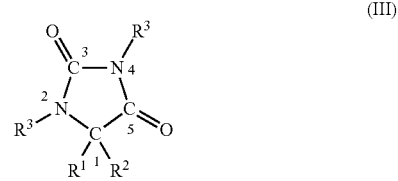

(III)

wherein the numerals attached to individual ring-constituting elements represent the positions of the ring-constituting elements; $R^1$ and $R^2$ are different from each other and each an organic group of 1 to 20 carbon atoms, or $R^1$ and $^2$ bond to each other to form a spiro ring of 3 to 20 carbon atoms bonding to the carbon of position 1; any of $R^1$, $R^2$ and the ring formed by bonding of $R^1$ and $R^2$ contains at least one asymmetric carbon atom; $R^3$ is one kind of protective group selected from the group consisting of tert-butyloxycarbonyl group, methoxycarbonyl group, phenoxycarbonyl group, benzyloxycarbonyl group, tert-butyldimethylsilyl group, tosyl group and benzenesulfonyl group; two $R^3$s may be different from each other.

Advantageous Effect

The method for producing a hydantoin ring compound of the present invention is a method of reacting a compound of the formula (I) used as a starting raw material, with a protective agent to form directly or indirectly "diastereomers each having one protective group" represented by the formula (II) and then making one "diastereomer having one protective group" of the "diastereomers each having one protective group" selectively precipitated. The hydantoin ring compound obtained in the present production method by elimination of the protective group of one "diastereomer having one protective group" is high in isomer purity.

Also, in the above method, the purity of the isomer obtained can be enhanced by simple crystallization without using a purification means such as column chromatography which is small in treating amount and which is a complicated separation means. Therefore, the present production method is useful industrially.

BEST MODE FOR CARRYING OUT THE INVENTION

The present invention is described in detail below.

The starting raw material used in the present method for producing a compound having a hydantoin ring is a compound represented by the following formula (I).

[Formula 6]

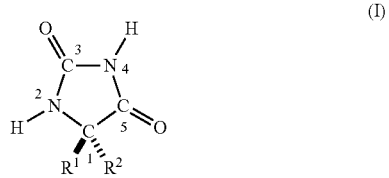

(I)

In formula (I), the numerals attached to individual ring-constituting elements represent the positions of the ring-constituting elements.

$R^1$ and $R^2$ are different from each other and each is an organic group of 1 to 20 carbon atoms, or $R^1$ and $R^2$ bond to each other to form a spiro ring of 3 to 20 carbon atoms bonding to the carbon of position 1.

Any of $R^1$, $R^2$ and the ring formed by bonding of $R^1$ and $R^2$ contains at least one asymmetric carbon atom. Owing to the presence of the plurality of asymmetric carbons, a pair of diastereomers are present in the compound of the chemical formula (I). That is, there are present a pair of diastereomers each having a diastereo-face containing the position 1 asymmetric carbon of the above chemical formula (I) and at least one asymmetric carbon present in any of $R^1$, $R^2$ and the ring formed by bonding of $R^1$ and $R^2$.

As the organic group of $R^1$ or $R^2$ containing no asymmetric atom, there can be mentioned, for example, hydroxy group, methoxy group, ethoxy group, propoxy group, isopropoxy group, cyclopropyl group, tert-butoxy group, benzyloxy group, methyl group, ethyl group, propyl group, isopropyl group, butyl group, isobutyl group, tert-butyl group, tert-butyloxycarbonyloxy group, benzyloxycarbonyloxy group, benzyloxycarboxyloxy group, methyloxycarbonyloxy group, trimethylsilyloxy group, tert-butyldimethylsilyloxy group, tosyloxy group, benzenesulfonyloxy group, mesyloxy group amino group, methylamino group, dimethylamino group, tert-butyloxycarbonylamino group, benzylamino group, benzyloxycarbonylamino group, trimethylsilylamino group, tert-butyldimethylsilylamino group, tosylamino group, benzenesulfonylamino group, mesylamino group, mercapto group, methylmercapto group, ethylmercapto group, glycidyl group, phenyl group, naphthyl group, thiazolyl group, isothiazolyl group, carboxyl group, methyloxycarboxyl group, ethyloxycarboxyl group, propyloxycarboxyl group, isopropyloxycarboxyl group, butyloxycarboxyl group, isobutyloxycarboxyl group, tert-butyloxycarboxyl group, carbamoyl group, hydrazinocarboxyl group, cyano group, nitro group, isocyano group, cyanate group, isocyanate group, thiocyanate group, isothiocyanate group, formyl group, oxo group, thioformyl group, thiocarboxyl group, dithiocarboxyl group, sulfonyl group, methanesulfonyl group, benzenesulfonyl group and tosyl group. The above organic groups may be bonded to each other. In the above organic groups, hydrogen atom may be substituted with halogen atom such as chlorine, bromine, fluorine, iodine or the like.

As the organic group of $R^1$ or $R^2$ containing asymmetric carbon atom, there can be mentioned, for example, 1-hydroxyethyl group, 1-hydroxypropyl group, 1-hydroxybutyl group, 1-hydroxypentyl group, 1-hydroxyhexyl group, 1-chloroethyl group, 1-chloropropyl group, 1-chlorobutyl group, 1-chloropentyl group, 1-chlorohexyl group, 1-bromoethyl group, 1-bromopropyl group, 1-bromobutyl group, 1-bromopentyl group, 1-bromohexyl group, 1-iodoethyl group, 1-iodopropyl group, 1-iodobutyl group, 1-iodopentyl group, 1-iodohexyl group, 1-nitroethyl group, 1-nitropropyl group, 1-nitrobutyl group, 1-nitropentyl group, 1-nitrohexyl group, 1-cyanoethyl group, 1-cyanopropyl group, 1-cyanobutyl group, 1-cyanopentyl group, 1-cyacnohexy group, 1-mercaptoethyl group, 1-mercapropropyl group, 1-mercaptobutyl group, 1-mercaptopentyl group, 1-mercaptohexyl group, 1-aminoethyl group, 1-aminopropyl group, 1-aminobutyl group, 1-aminopentyl group, 1-aminohexyl group, 1-methoxyethyl group, 1-methoxypropyl group, 1-methoxybutyl group, 1-methoxypentyl group, 1-methoxyhexyl group, 1-ethoxyethyl group, 1-ethoxypropyl group, 1-ethoxybutyl group, 1-ethoxypentyl group, 1-ethoxyhexyl group, 1-propoxyethyl group, 1-propoxypropyl group, 1-propoxybutyl group, 1-propoxypentyl group, 1-propoxyhexyl group, 2-hydroxypropyl group, 2-hydroxybutyl group, 2-hydroxypentyl group, 2-hydroxyhexyl group, 2-chloropropyl group, 2-chlorobutyl group, 2-chloropentyl group, 2-chlorohexyl group, 2-bromopropyl group, 2-bromobutyl group, 2-bromopentyl group, 2-bromohexyl group, 2-iodopropyl group, 2-iodobutyl group, 2-iodopentyl group, 2-iodohexyl group, 2-nitropropyl group, 2-nitrobutyl group, 2-nitropentyl group, 2-nitrohexyl group, 2-cyanopropyl group, 2-cyanobutyl group, 2-cyanopentyl group, 2-cyanohexyl group, 2-mercaptopropyl group, 2-mercaptobutyl group, 2-mercaptopentyl group, 2-mercaptohexyl group, 2-aminopropyl group, 2-aminobutyl group, 2-aminopentyl group, 2-aminohexyl group, 2-methoxypropyl group, 2-methoxybutyl group, 2-methoxypentyl group, 2-metoxyhexyl group, 2-ethoxypropyl group, 2-ethoxybutyl group, 2-etoxypentyl group, 2-ethoxyhexyl group, 2-propoxypropyl group, 2-propoxybutyl group, 2-propoxypentyl group, 2-propoxyhexyl group, 3-hydroxybutyl group, 3-hydroxypentyl group, 3-hydroxyhexyl group, 3-chlorobutyl group, 3-chloropentyl group, 3-chlorohexyl group, 3-bromobutyl group, 3-bromopentyl group, 3-bromohexyl group, 3-iodobutyl group, 3-iodopentyl group, 3-iodohexyl group, 3-nitrobbutyl group, 3-nitropentyl group, 3-nitrohexyl group, 3-cyanobutyl group, 3-cyanopentyl group, 3-cyanohexyl group, 3-mercaptobutyl group, 3-mercaptopentyl group, 3-mercaptohexyl group, 3-aminobutyl group, 3-aminopentyl group, 3-aminohexyl group, 3-methoxybutyl group, 3-methoxypentyl group, 3-methoxyhexyl group, 3-ethoxybutyl group, 3-ethoxypentyl group, 3-ethoxyhexyl group, 3-propoxybutyl group, 3-propoxypentyl group, 3-propoxyhexyl group, 4-hydroxypentyl group, 4-hydroxyhexyl group, 4-chloropentyl group, 4-chlorohexyl group, 4-bromopentyl group, 4-bromohexyl group, 4-iodopentyl group, 4-iodohexyl group, 4-nitrobutyl group, 4-nitropentyl group, 4-nitrohexyl group, 4-cyanopentyl group, 4-cyanohexyl group, 4-mercapropentyl group, 4-mercaptohexyl group, 4-aminobutyl group, 4-aminopentyl group, 4-aminohexyl group, 4-methoxypentyl group, 4-methoxyhexyl group, 4-ethoxypentyl group, 4-ethoxyhexyl group, 4-propoxypentyl group, 4-propoxyhexyl group, 1-glycidylethyl group, 1-glycidylpropyl group, 1-glycidylbutyl group, 1-glycidylpentyl group, 1-glycidylhexyl group, 2-glycidylpropyl group, 2-glydcidylbutyl group, 2-glycidylpentyl group, 2-glycidylhexyl group, 3-glydcidylbutyl group, 3-glycidylpentyl group, 3-glycidylhexyl group, 4-glycidylpentyl group, 4-glycidylhexyl group, 5-glycidylheyxl group, 1-phenylethyl group, 1-phenylpropyl group, 1-phenylbutyl group, 1-phenylpentyl group, 1-phenylhexyl group, 1-benzylethyl group, 1-benzylpropyl group, 1-benzylbutyl group, 1-benzylpentyl group, 1-benzylhexyl group, 1-phenoxyethyl group, 1-phenoxypropyl group, 1-phenoxybutyl group, 1-phenoxypentyl group and 1-phenoxyhexyl group.

The above organic groups may be bonded to each other. In these organic groups, at least one hydrogen atom may be substituted with hydroxy group, methoxy group, ethoxy group, propoxy group, isopropoxy group, cyclopropyl group, tert-butoxy group, benzyloxy group, methyl group, ethyl group, propyl group, isopropyl group, butyl group, isobutyl group, tert-butyl group, tert-butyloxycarbonyloxy group, benzyloxycarbonyloxy group, trimethylsilyloxy group, tert-butyldimethylsilyloxy group, tosyloxy group, benzenesulfonyloxy group, mesyloxy group amino group, methylamino group, dimethylamino group, tert-butyloxycarbonylamino group, benzylamino group, benzyloxycarbonylamino group, trimethylsilylamino group, tert-butyldimethylsilylamino group, tosylamino group, benzenesulfonylamino group and mesylamino group.

The carbon atoms of the ring formed by bonding of $R^1$ and $R^2$ is preferably 4 to 10 (include the position 1 carbon), more preferably 4 to 8.

As specific examples of the ring formed by bonding of $R^1$ and $R^2$, there can be mentioned cyclobutane, cycloheptane, cyclohexane, cyclooctane, cyclononane and cyclodecane, further cyclobutane, cycloheptane, cyclohexane, cyclooctane being preferred.

As described above, the ring formed by bonding of $R^1$ and $R^2$ has an asymmetric carbon atom. To the asymmetric carbon atom is bonded a substituent group other than hydrogen atom. As specific examples of the substituent group, there can be mentioned, for example, hydroxy group, methoxy group, ethoxy group, propoxy group, isopropoxy group, cyclopropyl group, tert-butoxy group, benzyloxy group, methyl group, ethyl group, propyl group, isopropyl group, butyl group, isobutyl group, tert-butyl group, tert-butyloxycarbonyloxy group, benzyloxycarbonyloxy group, trimethylsilyloxy group, tert-butyldimethylsilyloxy group, tosyloxy group, benzenesulfonyloxy group, mesyloxyamino group, methylamino group, dimethylamino group, tert-butyloxycarbonylamino group, benzylamino group, benzyloxycarbonylamino group, trimethylsilylamino group, tert-butyldimethylsilylamino group, tosylamino group, benzenesulfonylamino group and mesylamino group.

These substituent groups may be bonded to the plurality of carbons of the ring formed by bonding of $R^1$ and $R^2$. As particularly preferable substituent groups, there can be mentioned, for example, tert-butyloxycarbonyloxy group, benzyloxycarbonyloxy group, trimethylsilyloxy group, tert-butyldimethylsilyloxy group, methyloxycarbonyl group, benzyloxy group and hydroxy group.

The present invention is a method for selectively producing a compound having a hydantoin ring, represented by the above-shown formula (I), which is low in isomer content, by selectively separating one diastereomer of the one pair of diastereomers from a mixture of at least one pair of diastereomers having a structure represented by the formula (I).

The selective separation of one diastereomer of the one pair of diastereomers from the mixture comprises the following four steps as basic steps.

Step (1)

This step (1) is a step of reacting a mixture of the compounds having a hydantoin ring, represented by the formula (I), with a protecting agent in a solvent, to form directly or indirectly a mixture containing a pair of "diastereomers each having one protective group" represented by the following formula (II)

[formula 7]

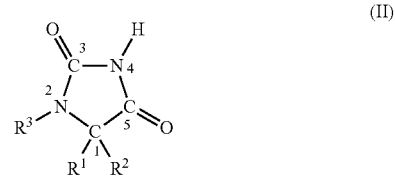

In the formula (II), the numerals attached to individual ring-constituting elements represent the positions of the ring-constituting elements; $R^1$ and $R^2$ have the same definitions as the $R^1$ and $R^2$ in the chemical formula (I); $R^3$ is one kind of protective group selected from the group consisting of tert-butyloxycarbonyl group, methoxycarbonyl group, phenoxycarbonyl group, benzyloxycarbonyl group, tert-butyldimethylsilyl group, tosyl group and benzenesulfonyl group.

The mixture of at least one pair of "diastereomers each having one protective group" having a structure represented by the formula (II) contains a pair of "diastereomers each having one protective group" each having a diastereo-face containing the position 1 asymmetric carbon of the above formula (II) and one asymmetric carbon present in any of $R^1$, $R^2$ and the ring formed by bonding of $R^1$ and $R^2$.

As the protecting agent, there can be used at least one kind of agent selected from the group consisting of di-tert-butyl dicarbonate, dimethyl carbonate, diphenyl carbonate, tert-butyloxycarbonyl chloride, tert-butyloxycarbonyl bromide, tert-butyloxycarbonyl fluoride, benzyloxycarbonyl chloride, tert-butyldimethylsilyl chloride, tosyl chloride and benzenesulfonyl chloride. Of these, particularly preferred is di-tert-butyl dicarbonate from the standpoint of introduction or elimination of protective group. The reaction for introduction of protective group is per se well known in the related technical field.

As the method of reacting the mixture of compounds each having a hydantoin ring, represented by the formula (I), with a protecting agent in a solvent to produce "diastereomers each having one protective group" represented by the formula (II), there are a method of directly introducing one protective group and a method of indirectly introducing one protective group.

In the method of directly introducing one protective group, a relatively small amount of a protecting agent is used for introduction of one protective group into the compounds of the formula (I) to complete the reaction (in the reaction, a large excess of the protecting agent is not reacted at one time). The addition amount of the protecting agent is determined appropriately depending upon the kinds of compounds, the conditions of reaction, etc. Ordinarily, the protecting agent is added in an amount of preferably 0.1 to 2.0 mols, more preferably 0.5 to 1.5 mols, particularly preferably 0.8 to 1.2 mols relative to 1 mol of the compounds of the formula (I).

In the method of indirectly introducing the protective group, firstly, the protective group is introduced into the nitrogen atoms of position 1 and position 4, of compound of the formula (I), to obtain "diastereomers each having two protective groups"; then, the protective group bonding to the position 4 nitrogen atom of each "diastereomer having two protective groups" is eliminated selectively. By this method, "diastereomers each having one protective group" can be produced indirectly.

In the production of "diastereomers each having two protective groups", the addition amount of protecting agent is determined appropriately depending upon the kinds of compounds, the conditions of reaction, etc. For example, the protecting agent is reacted in an amount of preferably more than 2 mols, more preferably 2.1 to 5.0 mols relative to 1 mol of the compounds of the formula (I).

The elimination of one protective group from each "diastereomer having two protective groups" is conducted by addition of a polar solvent into the reaction system. As the polar solvent preferred are protic solvents such as alcohol of 1 to 5 carbon atoms (e.g. methanol, ethanol, 1-propanol, 2-propanol, 1-butanol, 2-butanol, isobutanol, tert-butyl alcohol, amyl alcohol, sec-amyl alcohol or tert-amyl alcohol), water and the like. These protic solvents may be used singly or in combination of two or more kinds. There can also be used a mixture of a aprotic solvent (e.g. tetrahydrofuran, acetonitrile, acetone, methyl ethyl ketone, or methyl isobutyl ketone) and the above-mentioned protic solvent.

As to the addition amount of the polar solvent, there is no particular restriction. The addition amount may be at least one equivalent relative to the mols of the introduced protective group. The polar solvent may be added in a large excess when it functions also as a solvent. The reaction temperature when one protective group is eliminated, is preferably −78 to 150° C., more preferably −40 to 100° C. The reaction time is preferably 0.01 to 100 hours.

In the present invention, the method of indirectly producing "diastereomers each having one protective group" is preferably used because it can introduce the protective group reliably.

Step (2)

The step (2) is a step of, during and/or after the reaction of reacting the compounds of the formula (I) with a protecting agent, one "diastereomer having one protective group" of the pair of "diastereomers each having one protective group" is selectively precipitated from the mixture solution formed by the reaction.

The present inventor found that each of the pair of "diastereomers each having one protective group" has a different solubility in a certain solvent. As a result, the present inventor thought of method for making one of the pair of diastereomers selectively precipitated to purify the diastereomer.

As the solvent preferably used in the step in which the "diastereomer having one protective group" is selectively precipitated, there can be mentioned, for example, esters such as methyl acetate, ethyl acetate, propyl acetate, isopropyl acetate, butyl acetate, isobutyl acetate, tert-butyl acetate and the like; aliphatic hydrocarbons such as pentane, hexane, heptane, octane and the like; aromatic hydrocarbons such as toluene, xylene and the like; nitriles such as acetonitrile and the like; ketones such as acetone, methyl isobutyl ketone, methyl ethyl ketone and the like; ethers such as diethyl ether, tetrahydrofuran, tert-butyl methyl ether, dioxane and the like; alcohols such as methanol, ethanol, 1-propanol, 2-propanol, 1-butanol, 2-butanol, isobutanol, tert-butyl alcohol, amyl alcohol, sec-amyl alcohol, tert-amyl alcohol and the like; and water. These solvents may be used singly or in admixture of two or more kinds.

The solvent is appropriately selected and used depending upon the kind of the "diastereomer having one protective group" to be selectively precipitated, the conditions of separating-out, etc.

In case that one of the "diastereomers each having one protective group" is precipitated during the reaction is a case in which the compounds of the formula (I) are protected with a protecting agent to consecutively form one pair of "diastereomers each having one protective group" and, simultaneously therewith, consecutively one "diastereomer having one protective group" of the pair is selectively precipitated.

In case that one of the "diastereomers each having one protective group" is precipitated after the reaction is a case in which a time is needed up to the start of precipitation and the precipitation starts after the reaction has been completed substantially. It is considered that, in many cases, the above both cases may takes place simultaneously.

The reaction for introduction of protective group proceeds; the concentration of the pair of "diastereomers each having one protective group" becomes high and then exceeds the saturation concentration; as a result, precipitation starts spontaneously.

In the precipitation of one of the pair of "diastereomers each having one protective group", concentration, cooling or the like may be employed in combination.

Step (3)

The step (3) is a step of separating the precipitation product obtained in the step (2), from the reaction mixture solution, to obtain a compound represented by the formula (II), which is low in isomer content. As the method for separation, there can be mentioned, for example, filtration, centrifugation, decantation, etc.

Step (4)

The step (4) is a step of contacting the compound of the formula (II) low in isomer content, separated in the above step (3), with an acid to eliminate the protective group to obtain selectively one diastereomer of the compounds having a hydantoin ring, represented by the formula (I).

As to the acid used in this step, there is no particular restriction. As the acid, there can be mentioned, for example, mineral acids such as hydrochloric acid, sulfuric acid, nitric acid and the like; organic acids such as trifluoroacetic acid, methanesulfonic acid, trifluoromethanesulfonic acid, benzenesulfonic acid, p-toluenesulfonic acid, aminosulfonic acid and the like; and acids such as phosphoric acid, hydrogen bromide, hydrofluoric acid, hydrogen chloride. Hydrogen chloride may be used by dissolving in methanol, ethanol, dioxane, ethyl acetate or the like. These acids may be used singly or in combination of two or more kinds. The addition amount of the acid is preferably 1 to 5 mols, more preferably 2 to 4 mols relative to 1 mol of the protective group to be eliminated.

The reaction is conducted preferably in an organic solvent or in water. As the organic solvent used, there can be mentioned, for example, esters such as methyl acetate, ethyl acetate, propyl acetate, isopropyl acetate, butyl acetate, isobutyl acetate, tert-butyl acetate and the like; aliphatic hydrocarbons such as pentane, hexane, heptane, octane and the like; aromatic hydrocarbons such as toluene, xylene and the like; nitriles such as acetonitrile and the like; ketones such as acetone, methyl isobutyl ketone, methyl ethyl ketone and the like; ethers such as diethyl ether, tetrahydrofuran, tert-butyl methyl ether, dioxane and the like; and alcohols such as methanol, ethanol, 1-propanol, 2-propanol, 1-butanol, 2-butanol, isobutanol, tert-butyl alcohol, amyl alcohol, sec-amyl alcohol, tert-amyl alcohol and the like. These organic solvents and water may be used singly or in admixture of two or more kinds. The organic solvent or water used may be selected appropriately depending upon the kind of the compound having a hydantoin ring, which is to be obtained, the conditions of reaction, etc.

The reaction temperature for elimination of protective group is preferably a range of room temperature to the boiling point of organic solvent (including water), more preferably 78 to 150° C. The reaction time is preferably 0.01 to 100 hours, more preferably 0.1 to 50 hours. It is confirmed that, in the present invention, the elimination reaction of protective group (deprotection reaction) proceeds quantitatively and there is no change of paired isomers ratio in the reaction.

In the above-mentioned present method for producing a compound having a hydantoin ring, preferably comprises further a step (3') of purifying the compound represented by the formula (II), low in isomer content, obtained in the step (3). The step (3') is conducted preferably between the step (3) and the step (4).

As the step (3') for purification, there can be mentioned, for example, a crystallization method and a slurry method which is suspending the compound of the formula (II) in a solvent to dissolve the impurity contained in the compound to remove it. A step particularly preferred as the step (3') for purification, is a step comprising the following steps (3'-1), (3'-2) and (3'-3).

The step (3'-1) is a step of reacting the compound represented by the formula (II) low in isomer content, obtained in the step (3), with a protecting agent to obtain a mixture of at least one pair of "diastereomers each having two protective groups" each having a structure represented by the formula (III). The "diastereomers each having two protective groups" are compounds each having a diastereo-face containing the position 1 asymmetric carbon of the chemical formula (III) and one asymmetric carbon contained in any of $R^1$, $R^2$ and the ring formed by bonding of $R^1$ and $R^2$.

As the protecting agent, there is preferred at least one kind selected form the group consisting of di-tert-butyl dicarbonate, dimethyl carbonate, diphenyl carbonate, tert-butyloxycarbonyl chloride, tert-butyloxycarbonyl bromide, tert-butyloxycarbonyl fluoride, benzyloxycarbonyl chloride, tert-butyldimethylsilyl chloride, tosyl chloride and benzenesulfonyl chloride. The reaction conditions for introducing two protective groups, etc. are the same as mentioned previously.

In the step (3'-2), there are selectively eliminated the protective group bonding to the position 4 nitrogen atom of each "diastereomer having two protective groups" contained in the mixture obtained in the step (3'-1).

By this reaction is formed a mixture of at least one pair of "diastereomers each having one protective group" having a structure represented by the formula (II), which mixture contains a pair of "diastereomers each having one protective group", and each having a diastereo-face containing the position 1 asymmetric carbon of the above formula (II) and one asymmetric carbon present in any of $R^1$, $R^2$ and the ring formed by bonding of $R^1$ and $R^2$. The conditions of elimination reaction, etc. are the same as mentioned previously.

In the step (3'-3), during and/or after the above reaction in the step (3'-2), there is selective precipitation of one "diastereomer having one protective group" of the pair of "diastereomers each having one protective group" from the mixture solution formed by the reaction. The conditions of selective precipitation, such as the solvent used, etc. are the same as mentioned previously.

By incorporating the above step (3') into the present production method, a hydantoin ring compound having higher isomer purity can be produced.

EXAMPLES

The present invention is described more specifically below by way of Examples. Hereinafter, the following abbreviations are used in some cases; that is, Boc for tert-butyloxycarbonyl group, Cbz for benzyloxycarbonyl, TBDMS for tert-butyldimethylsilyl group, and Tos for p-toluenesulfonyl group.

Reference Example 1

(Synthesis of (Z)-2-benzyloxy-5,7-diazaspiro[3,4]
octane-6,8-dione and (E)-2-benzyloxy-5,7-diazaspiro
[3,4]octane-6,8-dione)

The reaction formula is shown below.

[Formula 8]

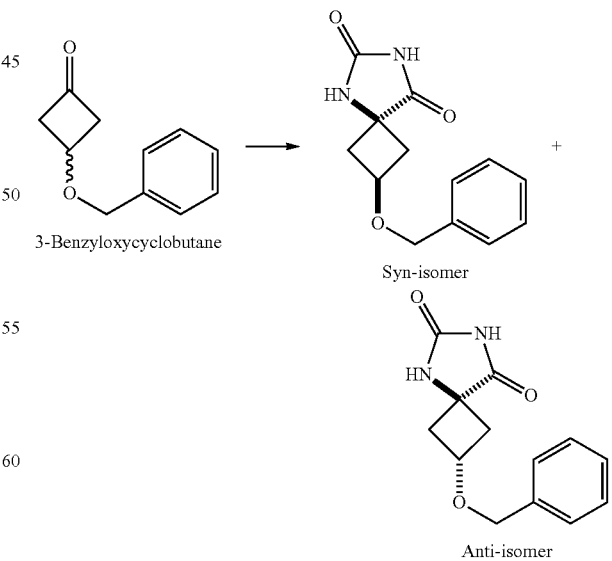

To a 20-liter, four-necked separable flask were fixed a thermometer, a condenser and a stirrer. In the flask was placed a solution of 1,250 g (13 mols) of ammonium carbonate and 278 g (5.2 mols) of ammonium chloride dissolved in 9 liters of deinozized water. In the flask was further placed 236 g (1.3 mols) of 3-benzyloxycyclobutanone dissolved in 9 liters of ethanol. Stirring was conducted at 25° C. for 30 minutes. Then, 380 g (5.8 mols) of potassium cyanide was placed in the flask, followed by stirring at 60° C. for 12 hours.

After the completion of the reaction, the solvent (including water) was distilled off to obtain a dry reaction product as a yellow solid. The solid was mixed with 10 liters of deionized water, stirring was conducted for 1 hour, and the mixture was subjected to solid-liquid separation. The wet material obtained was dried at 60° C. for 12 hours to obtain 164 g (yield: 51%) of a mixture of (Z)-2-benzyloxy-5,7-diazaspiro[3,4]octane-6,8-dione (syn-isomer) and (E)-2-benzyloxy-5,7-diazaspiro[3,4]octane-6,8-dione (anti-isomer) [hereinafter, the mixture is referred to as mixture (A)]. Analysis by high performance liquid chromatography (HPLC) indicated syn-isomer/anti-isomer=80/20. The column used was Inertsil ODS-3 (trade name) (ODS type) produced by GL Science. The eluent was acetonitrile/phosphoric acid buffer=½ (v/v). Incidentally, the phosphoric acid buffer was an aqueous solution containing 20 mmols/liter of potassium dihydrogenphosphate.

Example 1

DiBoc Isomer and Production Thereof

Using the mixture (A) of (Z)-2-benzyloxy-5,7-diazaspiro[3,4]octane-6,8-dione (syn-isomer) and (E)-2-benzyloxy-5,7-diazaspiro[3,4]octane-6,8-dione (anti-isomer) which were produced in Reference Example 1, di-tert-butyl esters thereof (diBoc isomers) were produced. The reaction formula is shown below.

[Formula 9]

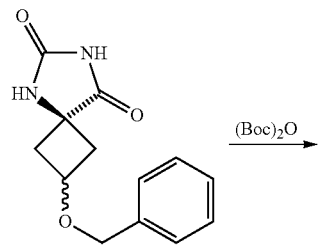

Mixture (A)

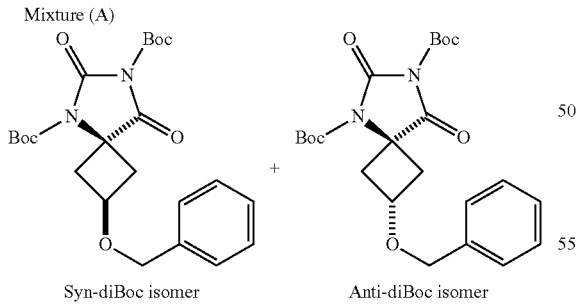

Syn-diBoc isomer      Anti-diBoc isomer 8.4 g (34 mmols) of the mixture (A) obtained in Reference Example 1 was placed in a 100-ml of four-necked flask provided with a thermometer, a condenser and a stirrer. 45 g of ethyl acetate and 0.25 g (2.2 mmols) of 4-dimethylaminopyridine were added, followed by stirring. Then, 21.8 g (100 mmols) of di-tert-butyl dicarbonate was added in the flask, followed by stirring at 40° C. for 7 hours. After the completion of the reaction, the solvent was distilled off to obtain an oily matter.

The oily matter was separated into two components by silica gel chromatography to obtain respective components. ¹H-NMR and elemental analysis indicated that the two components obtained were (Z)-2-benzyloxy-6,8-dioxo-5,7-diazaspiro[3,4]octane-5,7-dicarboxylic acid di-tert-butyl ester (syn-diBoc isomer) and (E)-2-benzyloxy-6,8-dioxo-5,7-diazaspiro[3,4]octane-5,7-dicarboxylic acid di-tert-butyl ester (anti-diBoc isomer) (the result of ¹H-NMR is shown below and the result of elemental analysis is shown in Tables 1 and 2).

The yield of the di-tert-butyl ester of (Z)-2-benzyloxy-6,8-dioxo-5,7-diazaspiro[3,4]octane-5,7-dicarboxylic acid (syn-diBoc isomer) was 9.2 g (yield 60%) and the yield of the di-tert-butyl ester of (E)-2-benzyloxy-6,8-dioxo-5,7-diazaspiro[3,4]octane-5,7-dicarboxylic acid (anti-diBoc isomer) was 2.3 g (yield 15%). No impurity was found in each component.

Syn-diBoc Isomer

[Formula 10]

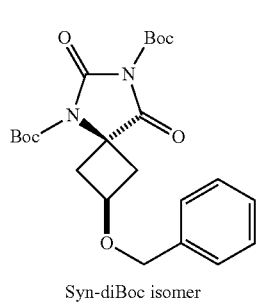

Syn-diBoc isomer

<¹H-NMR>
σ 1.56 (18H, s), 2.74 (2H, m), 3.02 (2H, m), 4.49 (3H, m), 7.38 (5H, m)

TABLE 1

| | Elemental analysis | | | |
|---|---|---|---|---|
| | C | H | N | Total |
| Theoretical value | 61.87% | 6.77% | 6.27% | 74.91% |
| Measured value | 61.67% | 6.97% | 8.17% | 74.81% |

Anti-diBoc Isomer

[Formula 11]

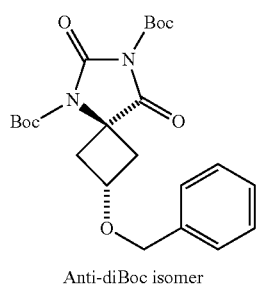

Anti-diBoc isomer

<¹H-NMR>
σ 1.50 (18H, s), 2.54 (2H, m), 2.86 (2H, m), 4.39 (3H, m), 7.35 (5H, m)

TABLE 2

| | Elemental analysis | | | |
|---|---|---|---|---|
| | C | H | N | Total |
| Theoretical value | 61.87% | 6.77% | 6.27% | 74.91% |
| Measured value | 61.66% | 6.98% | 8.19% | 74.83% |

Example 2

Syn-monoBoc Isomer and Production Thereof
(Indirect Method)

Using the mixture (A) of (Z)-2-benzyloxy-5,7-diazaspiro[3,4]octane-6,8-dione (syn-isomer) and (E)-2-benzyloxy-5,7-diazaspiro[3,4]octane-6,8-dione (anti-isomer), produced in Reference Example 1, di-tert-butyl esters thereof (diBoc isomers) were produced. The di-tert-butyl esters were converted into mono-tert-butyl esters (monoBoc isomers). Precipitation was conducted from the reaction mixture to obtain a syn-monoBoc isomer of the mono-tert-butyl esters selectively.

Then, the tert-butyloxycarbonyl group of the syn-monoBoc isomer was eliminated to obtain (Z)-2-benzyloxy-5,7-diazaspiro[3,4]octane-6,8-dione (syn-isomer).

The reaction formula is shown below.

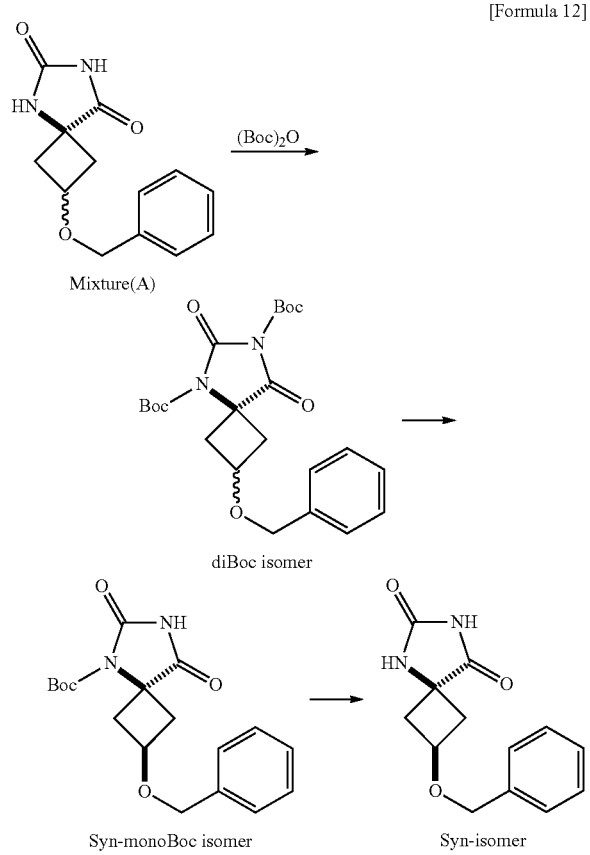

Production of diBoc Isomers 84 g (0.34 mol) of the mixture (A) obtained in Reference Example 1 was placed in a 1-liter, four-necked flask provided with a thermometer, a condenser and a stirrer. 450 g of ethyl acetate and 2.5 g (0.022 mol) of 4-dimethylaminopyridine were added, followed by stirring. Then, 148.9 g (0.682 mol) of di-tert-butyl dicarbonate was added in the flask, followed by stirring at 40° C. for 7 hours to give rise to a reaction to obtain a reaction mixture containing diBoc isomers.

Selective Crystallization of Syn-monoBoc Isomer

To the above reaction mixture was added 84 g of methanol. The mixture was stirred at 40° C. for 7 hours and then cooled to 10° C. The resulting crystal was precipitated by solid-liquid separation, rinsed with 90 g of ethyl acetate, and dried at 40° C. for 12 hours to obtain a white crystal. 1H-NMR and elemental analysis identified that the white crystal was (Z)-2-benzyloxy-6,8-dioxo-5,7-diazaspiro[3,4]octane-5-carboxylic acid tert-butyl ester (syn-monoBoc isomer) (the result of $^1$H-NMR is shown below and the result of elemental analysis is shown in Table 3). The yield was 88.0 g (yield 74.7%) and the purity by HPLC analysis was 97%.

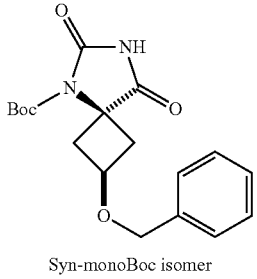

Syn-monoBoc isomer

<$^1$H-NMR>

σ 1.60 (9H, s), 2.65 (2H, m), 3.01 (2H, m), 4.15 (1H, m), 4.48 (2H, s), 7.36 (5H, m), 11.51 (1H, s)

TABLE 3

| | Elemental analysis | | | |
|---|---|---|---|---|
| | C | H | N | Total |
| Theoretical value | 62.42% | 6.40% | 8.08% | 76.90% |
| Measured value | 62.40% | 6.38% | 8.18% | 77.00% |

The obtained (Z)-2-benzyloxy-6,8-dioxo-5,7-diazaspiro[3,4]octane-5-carboxylic acid tert-butyl ester (syn-monoBoc isomer) was purified by silica gel column chromatography.

The impurity eluted was collected. The impurity was (E)-2-benzyloxy-6,8-dioxo-5,7-diazaspiro[3,4]octane-5-carboxylic acid tert-butyl ester (anti-monoBoc isomer). The $^1$H-NMR result of the anti-monoBoc isomer is shown below and the elemental analysis result is shown in Table 4.

In the (Z)-2-benzyloxy-6,8-dioxo-5,7-diazaspiro[3,4]octane-5-carboxylic acid tert-butyl ester (syn-monoBoc isomer) before purification by column chromatography, the syn-isomer/anti-isomer ratio was 97/3 and there was no other impurity.

[Formula 14]

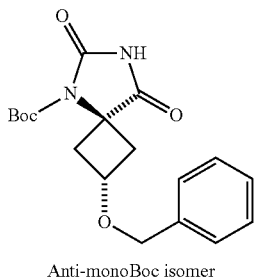

Anti-monoBoc isomer

<¹H-NMR>
σ 1.48 (9H, s), 2.53 (2H, m), 2.82 (2H, m), 4.40 (3H, m), 7.36 (5H, m), 11.38 (1H, s)

TABLE 4

| | Elemental analysis | | | |
|---|---|---|---|---|
| | C | H | N | Total |
| Theoretical value | 62.42% | 6.40% | 8.08% | 76.90% |
| Measured value | 62.32% | 6.50% | 8.18% | 77.00% |

Production of Syn-Isomer 1.0 g (2.89 mmols) of the above-obtained (Z)-2-benzyloxy-6,8-dioxo-5,7-diazaspiro[3,4]octane-5-carboxylic acid tert-butyl ester (syn-monoBoc isomer) containing 3% of the anti-monoBoc isomer) was placed in a 50-ml, four-necked flask provided with a thermometer, a condenser and a stirrer. 5 ml of ethyl acetate and 1 ml of 4 N-hydrogen chloride ethyl acetate solution were added, followed by stirring at 50° C. for 4 hours. Then, the solvent was distilled off to obtain a dry white crystal. The white crystal was (Z)-2-benzyloxy-5,7-diazaspiro[3,4]octane-6,8-dione (syn-isomer). The yield was 0.7 g (yield 98.4%). The HPLC analysis thereof identified syn-isomer/anti-isomer=97/3.

Example 3

Purification by Duplicated Conversion into diBoc Isomers

This purification corresponds to the steps (3'-1), (3'-2) and (3'-3).

8.4 g (0.034 mol) of the (Z)-2-benzyloxy-6,8-dioxo-5,7-diazaspiro[3,4]octane-5-carboxylic acid tert-butyl ester (syn-monoBoc isomer) containing 3% of the anti-isomer, obtained in Example 2 was placed in a 100-ml, four-necked flask provided with a thermometer, a condenser and a stirrer. 45 g of ethyl acetate and 0.25 g (0.0022 mol) of 4-dimethylaminopyridine were added into the flask, followed by stirring. Then, 7.5 g (0.0341 mol) of di-tert-butyl dicarbonate was added, followed by stirring at 40° C. for 7 hours.

After the reaction, 8.4 g of methanol was added to the reaction mixture, followed by stirring at 40° C. for 7 hours. Then, the reaction mixture was cooled to 10° C. The precipitated crystal was obtained by solid-liquid separation. The crystal separated was rinsed with 9.0 g of ethyl acetate, followed by drying at 40° C. for 12 hours. The resulting white crystal was (Z)-2-benzyloxy-6,8-dioxo-5,7-diazaspiro[3,4] octane-5-carboxylic acid tert-butyl ester (syn-monoBoc isomer). The yield was 6.9 g (yield 82.0%) and the result of HPLC analysis was syn-isomer/anti-isomer=99.5/0.5.

[Formula 15]

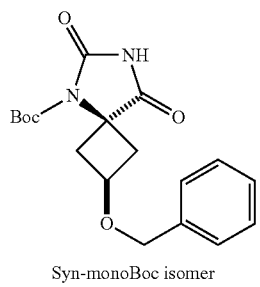

Syn-monoBoc isomer

Example 4

Purification Using Slurry

This purification corresponds to the step (3').

8.4 g (0.034 mol) of the (Z)-2-benzyloxy-6,8-dioxo-5,7-diazaspiro[3,4]octane-5-carboxylic acid tert-butyl ester (syn-monoBoc isomer) containing 3% of the anti-isomer, obtained in Example 2 was placed in a 100-ml, four-necked flask provided with a thermometer, a condenser and a stirrer. Further, 45 g of ethyl acetate was placed in the flask. Refluxing was conducted in a slurry state for 2 hours, with stirring. Then, the flask contents were cooled to 10° C. and the resulting crystal was obtained by solid-liquid separation. The crystal was rinsed with 9.0 g of ethyl acetate and then dried at 40° C. for 12 hours.

The white crystal obtained was (Z)-2-benzyloxy-6,8-dioxo-5,7-diazaspiro[3,4]octane-5-carboxylic acid tert-butyl ester (syn-monoBoc isomer). The yield was 7.6 g (yield 90.0%) and the result of HPLC analysis was syn-isomer/anti-isomer=99.0/1.0.

[Formula 16]

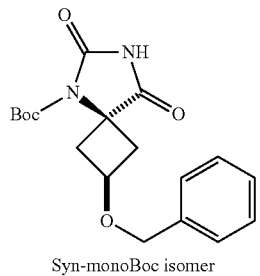

Syn-monoBoc isomer

Example 5

Purification by Recrystallization

This purification corresponds to the step (3').

8.4 g (0.034 mol) of the (Z)-2-benzyloxy-6,8-dioxo-5,7-diazaspiro[3,4]octane-5-carboxylic acid tert-butyl ester (syn-monoBoc isomer) containing 3% of the anti-isomer, obtained in Example 2 was placed in a 100-ml, four-necked flask provided with a thermometer, a condenser and a stirrer. Further, 340 g of ethyl acetate was added in the flask. Refluxing was conducted in a uniform solution state for 2 hours, with stirring. Then, the contents in the flask were cooled to 10° C.

for crystallization. The resulting crystal was obtained by solid-liquid separation. The crystal was rinsed with 9.0 g of ethyl acetate and then dried at 40° C. for 12 hours. The white crystal obtained was (Z)-2-benzyloxy-6,8-dioxo-5,7-diazaspiro[3,4]octane-5-carboxylic acid tert-butyl ester (syn-isomer). The yield was 6.9 g (yield 82.0%) and the result of HPLC analysis was syn-isomer/anti-isomer=99.3/0.7.

[Formula 17]

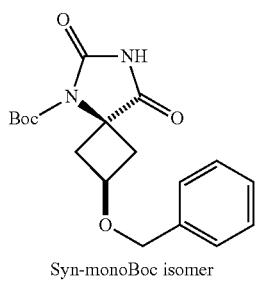

Syn-monoBoc isomer

Example 6

Elimination of Boc Group (Removal of Boc Group)

The reaction formula is shown below.

[Formula 18]

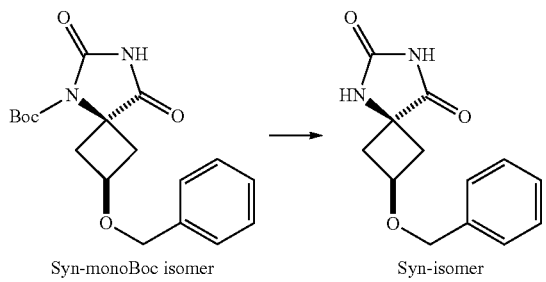

Syn-monoBoc isomer → Syn-isomer 1.0 g (2.89 mmols) of the (Z)-2-benzyloxy-6,8-dioxo-5,7-diazaspiro[3,4]octane-5-carboxylic acid tert-butyl ester (syn-monoBoc isomer) containing 0.5% of the anti-isomer, obtained in Example 3 was placed in a 50-ml, four-necked flask provided with a thermometer, a condenser and a stirrer. Further, 5 ml of ethyl acetate and 1 ml of a 4 N hydrogen chloride ethyl acetate solution were added, followed by stirring at 50° C. for 4 hours. Then, the solvent was distilled off to obtain a dry reaction product as a white crystal. The white crystal was (Z)-2-benzyloxy-5,7-diazaspiro[3,4]octane-6,8-dione (syn-isomer). The yield was 0.7 g (yield 98.4%) and the result of HPLC analysis was syn-isomer/anti-isomer=99.5/0.5.

Example 7

Direct Method

In the step (1), the mixture (A) of diastereomers was reacted with a protecting agent in a solvent and the syn-monoBoc isomer obtained was precipitated directly. The reaction formula is shown below.

[Formula 19]

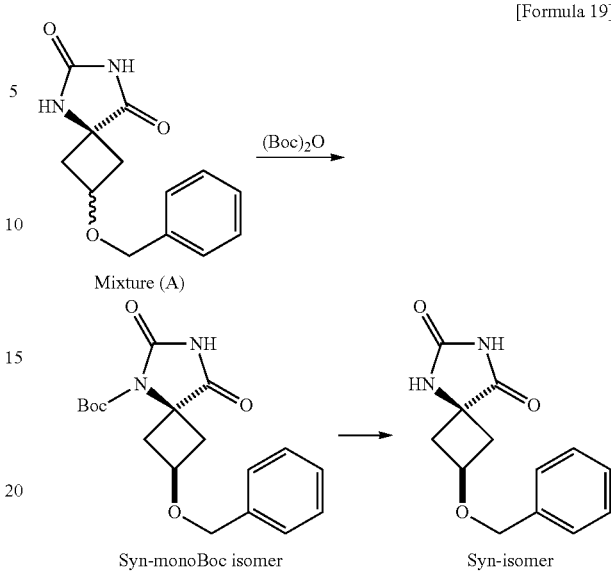

Mixture (A) → Syn-monoBoc isomer → Syn-isomer 8.4 g (34 mmols) of the mixture (A) obtained in Reference Example 1 was placed in a 1-liter, four-necked flask provided with a thermometer, a condenser and a stirrer. 45 g of ethyl acetate and 0.25 g (2.2 mmols) of 4-dimethylaminopyridine were added, followed by stirring. Further, 11.9 g (54.4 mols) of di-tert-butyl dicarbonate was added, followed by stirring at 25° C. for 10 hours. The precipitated crystal was obtained by solid-liquid separation. The crystal was rinsed with 9 g of ethyl acetate and then dried at 40° C. for 12 hours. The white crystal obtained was (Z)-2-benzyloxy-6,8-dioxo-5,7-diazaspiro[3,4]octane-5-carboxylic acid tert-butyl ester (syn-monoBoc isomer). The yield was 3.5 g (yield 30.0%) and the result of HPLC analysis was syn-isomer/anti-isomer=97/3.

1.0 g (2.89 mmols) of the above-obtained (Z)-2-benzyloxy-6,8-dioxo-5,7-diazaspiro[3,4]octane-5-carboxylic acid tert-butyl ester (syn-monoBoc isomer) containing 3% of the anti-isomer was placed in a 50-ml, four-necked flask provided with a thermometer, a condenser and a stirrer. 5 ml of ethyl acetate and 1 ml of a 4 N hydrogen chloride ethyl acetate solution were added, followed by stirring at 50° C. for 4 hours. Then, the reaction mixture was subjected to distillation to remove the solvent to obtain a dry product. The white crystal obtained was (Z)-2-benzyloxy-5,7-diazaspiro[3,4]octane-6,8-dione (syn-isomer). The yield was 0.7 g (yield 98.4%) and the result of HPLC analysis was syn-isomer/anti-isomer=99.5/0.5.

Example 8

Indirect Method (Case of Using No Methanol)

[Formula 20]

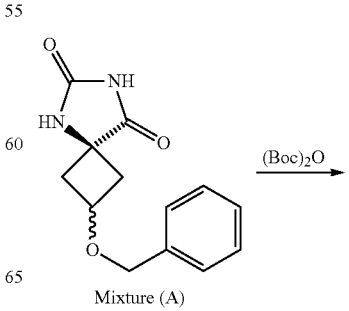

Mixture (A)

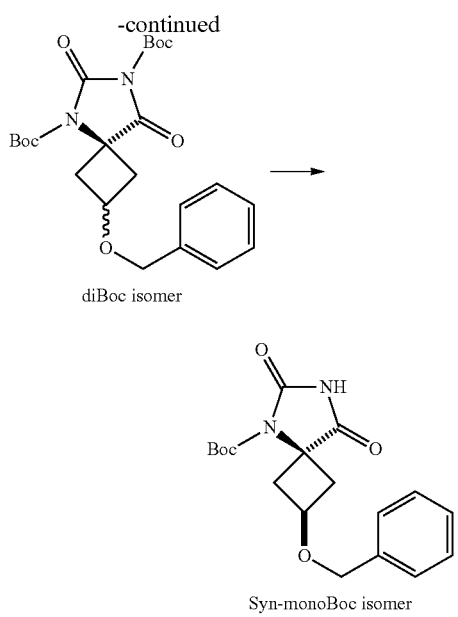

diBoc isomer

Syn-monoBoc isomer 8.4 g (34 mmols) of the mixture (A) obtained in Reference Example 1 was placed in a 1-liter, four-necked flask provided with a thermometer, a condenser and a stirrer. 45 g of ethyl acetate and 0.25 g (2.2 mmols) of 4-dimethylaminopyridine were added, followed by stirring. 14.9 g (68.2 mols) of di-tert-butyl dicarbonate was added, followed by stirring at 40° C. for 7 hours, which gave a uniform solution.

Further, stirring was conducted at 50° C. for one week, whereby precipitation of a crystal was confirmed. Then, the mixture was cooled to 10° C. The crystal was obtained by solid-liquid separation, rinsed with 9 g of ethyl acetate, and dried at 40° C. for 12 hours to obtain a white crystal. The white crystal obtained was (Z)-2-benzyloxy-6,8-dioxo-5,7-diazaspiro[3,4]octane-5-carboxylic acid tert-butyl ester (syn-monoBoc isomer). The yield was 58.9 g (50%) and the result of HPLC analysis was syn-isomer/anti-isomer=96/4.

Examples 9 to 16

Each syn-monoBoc isomer was produced according to the operation described in Example 2 except that the conditions shown in Table 5 were employed. Incidentally, di-tert-butyl dicarbonate is abbreviate for (Boc)₂O.

Example 17

Production Method of diBoc Isomers Using tert-butyloxycarbonyl Fluoride

[Formula 21]

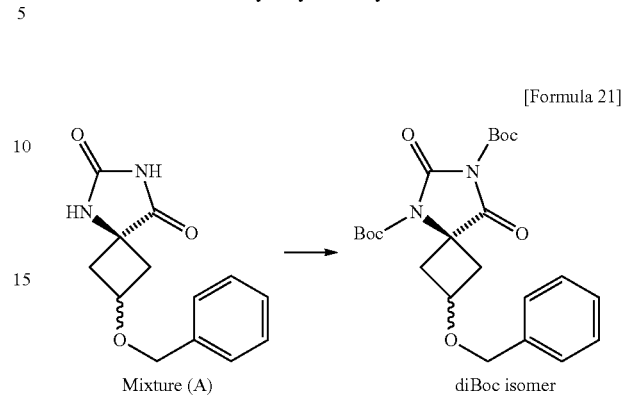

Mixture (A) → diBoc isomer 8.4 g (34 mmols) of the mixture (A) obtained in Reference Example 1 was placed in a 100-ml, four-necked flask provided with a thermometer, a condenser and a stirrer. 45 g of tetrahydrofuran was added, followed by stirring with cooling at −40° C. Then, 42.5 ml (68 mmols) of a hexane solution containing 1.6 mols/liter of n-butyl lithium, followed by stirring at −20° C. for 1 hour. Then, 7.7 g (68 mmols) of tert-butyloxycarbonyl fluoride was added, followed by stirring at 10° C. for 1 hour. After the completion of the reaction, 30 g of a 15% aqueous sodium chloride solution was added. After removal of the aqueous layer, the tetrahydrofuran layer was concentrated to obtain an oily matter.

The oily matter was separated into two components by silica gel chromatography to obtain respective components. $^1$H-NMR measurement and elemental analysis confirmed that the two components obtained were (Z)-2-benzyloxy-6,8-dioxo-5,7-diazaspiro[3,4]octane-5,7-dicarboxylic acid di-tert-butyl ester (syn-diBoc isomer) and (E)-2-benzyloxy-6,8-dioxo-5,7-diazaspiro[3,4]octane-5,7-dicarboxylic acid di-tert-butyl ester (anti-diBoc isomer). The yield of (Z)-2-benzyloxy-6,8-dioxo-5,7-diazaspiro[3,4]octane-5,7-dicarboxylic acid di-tert-butyl ester (syn-diBoc isomer) was 9.2 g (yield 60%) and the yield of (E)-2-benzyloxy-6,8-dioxo-5,7-diazaspiro[3,4]octane-5,7-dicarboxylic acid di-tert-butyl ester (anti-diBoc isomer) was 2.3 g (yield 15%). There was no other impurity in each component. Incidentally, the results of $^1$H-NMR and elemental analysis were the same as in Example 1.

TABLE 5

Results of Examples 9 to 16

| Examples | (Boc)₂O | Solvent | Reaction temp. | Polar solvent | Crystallization temp. | Syn-isomer yield (%) | Anti-isomer Yield (%) |
|---|---|---|---|---|---|---|---|
| 9 | 1.9 eq. | Butyl acetate | 50° C. | 2-Propanol | 0° C. | 70% | 3% |
| 10 | 2.2 eq. | Toluene | 60° C. | Ethanol | 5° C. | 65% | 4% |
| 11 | 3.0 eq. | Acetone | 30° C. | 2-Butyl alcohol | 10° C. | 80% | 4% |
| 12 | 1.9 eq. | Methylene chloride | 40° C. | 1-Butyl alcohol | 0° C. | 70% | 4% |
| 13 | 2.2 eq. | THF | 67° C. | Water | 5° C. | 65% | 5% |
| 14 | 3.0 eq. | Heptane | 40° C. | Ethanol | 10° C. | 80% | 5% |
| 15 | 5.0 eq. | Diethyl ether | 35° C. | Methanol | 10° C. | 70% | 4% |
| 16 | 2.2 eq. | Ethyl acetate/Tert-BuOH = 2/1 | 67° C. | water | 5° C. | 65% | 3% |

Example 18

Case of Using Benzyloxycarbonyl Chloride as Protecting Agent

[Formula 22]

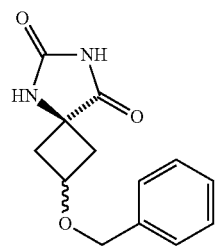

Mixture (A)

→

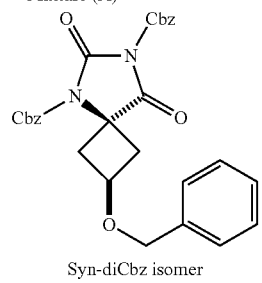   +   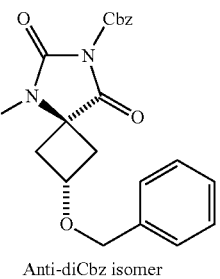

Syn-diCbz isomer        Anti-diCbz isomer

An operation was conducted according to that of Example 17 except that benzyloxycarbonyl chloride was used in place of the tert-butyloxycarbonyl fluoride used in Example 17.

The oily matter obtained was separated into two components by silica gel chromatography to obtain respective components. LC-MS analysis and elemental analysis confirmed that the two components obtained were (Z)-2-benzyloxy-6,8-dioxo-5,7-diazaspiro[3,4]octane-5,7-dicarboxylic acid dibenzyl ester (syn-diCbz isomer) and (E)-2-benzyloxy-6,8-dioxo-5,7-diazaspiro[3,4]octane-5,7-dicarboxylic acid dibenzyl ester (anti-diCbz isomer).

The yield of (Z)-2-benzyloxy-6,8-dioxo-5,7-diazaspiro[3,4]octane-5,7-dicarboxylic acid dibenzyl ester(syn-diCbz isomer) was 9.6 g (yield 55%) and the yield of (E)-2-benzyloxy-6,8-dioxo-5,7-diazaspiro[3,4]octane-5,7-dicarboxylic acid di-tert-butyl ester (anti-diCbz isomer) was 1.7 g (yield 10%). There was no other impurity in each component. The result of LC-MS is shown below and the result of elemental analysis is shown in Table 6 and Table 7.

Syn-diCbz Isomer

[Formula 23]

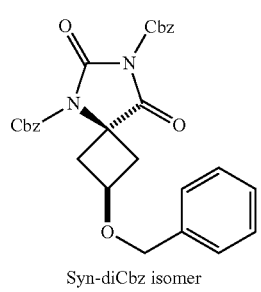

Syn-diCbz isomer

\<LC-MS\>

Molecular weight 514 was confirmed by LC-MS analysis.

TABLE 6

| | \multicolumn{4}{c}{Elemental analysis} | | | |
|---|---|---|---|---|
| | C | H | N | Total |
| Theoretical value | 67.70% | 5.09% | 5.44% | 78.23% |
| Measured value | 67.50% | 5.29% | 5.54% | 78.33% |

Anti-diCbz Isomer

[Formula 24]

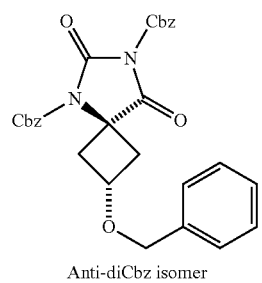

Anti-diCbz isomer

\<LC-MS\>

Molecular weight 514 was confirmed by LC-MS analysis.

TABLE 7

| | C | H | N | Total |
|---|---|---|---|---|
| Theoretical value | 67.70% | 5.09% | 5.44% | 78.23% |
| Measured value | 67.65% | 5.14% | 5.49% | 78.28% |

Example 19

Case of Using p-toluenesulfonyl Chloride as Protecting Agent

[Formula 25]

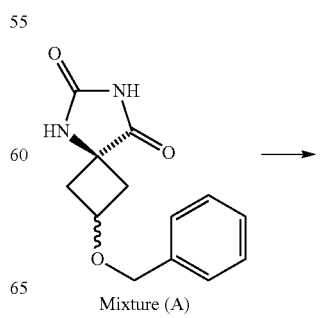

Mixture (A)

→

-continued

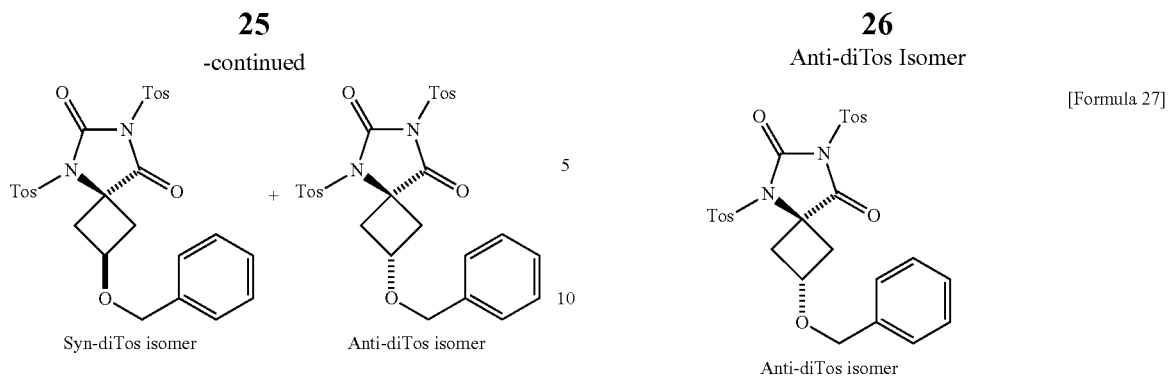

Syn-diTos isomer      Anti-diTos isomer

An operation was conducted according to that of Example 17 except that p-toluenesulfonyl chloride was used in place of the tert-butyloxycarbonyl fluoride used in Example 17.

The oily matter obtained was separated into two components by silica gel chromatography to obtain respective components. LS-MS analysis and elemental analysis confirmed that the two components obtained were (Z)-2-benzyloxy-6,8-dioxo-5,7-diazaspiro[3,4]octan-yl-5,7-di-p-methylphenylsulfone (syn-diTos isomer) and (E)-2-benzyloxy-6,8-dioxo-5,7-diazaspiro[3,4]octan-yl-5,7-di-p-methylphenylsulfone (anti-diTos isomer). The yield of (Z)-2-benzyloxy-6,8-dioxo-5,7-diazaspiro[3,4]octan-yl-5,7-di-p-methylphenylsulfone (syn-diTos isomer) was 10.9 g (yield 58%) and the yield of (E)-2-benzyloxy-6,8-dioxo-5,7-diazaspiro[3,4]octan-yl-5,7-di-p-methylphenylsulfone (anti-diTos isomer) was 2.4 g (13%). There was no other impurity in each component. The result of LC-MS is shown below and the result of elemental analysis is shown in Tables 8 and 9.

Syn-diTos Isomer

[Formula 26]

Syn-diTos isomer

<LC-MS>

Molecular weight 554 was confirmed by LC-MS analysis.

TABLE 8

| | Elemental analysis | | | | |
|---|---|---|---|---|---|
| | C | H | N | S | Total |
| Theoretical value | 58.47% | 4.73% | 5.05% | 11.56% | 79.81% |
| Measured value | 58.32% | 4.88% | 5.10% | 11.36% | 79.71% |

Anti-diTos Isomer

[Formula 27]

Anti-diTos isomer

<LC-MS>

Molecular weight 554 was confirmed by LC-MS analysis.

TABLE 9

| | Elemental analysis | | | | |
|---|---|---|---|---|---|
| | C | H | N | S | Total |
| Theoretical value | 58.47% | 4.73% | 5.05% | 11.56% | 79.81% |
| Measured value | 58.67% | 4.53% | 5.15% | 11.36% | 79.91% |

Example 20

Case of Using tert-butyldimethylsilyl Chloride as Protecting Agent

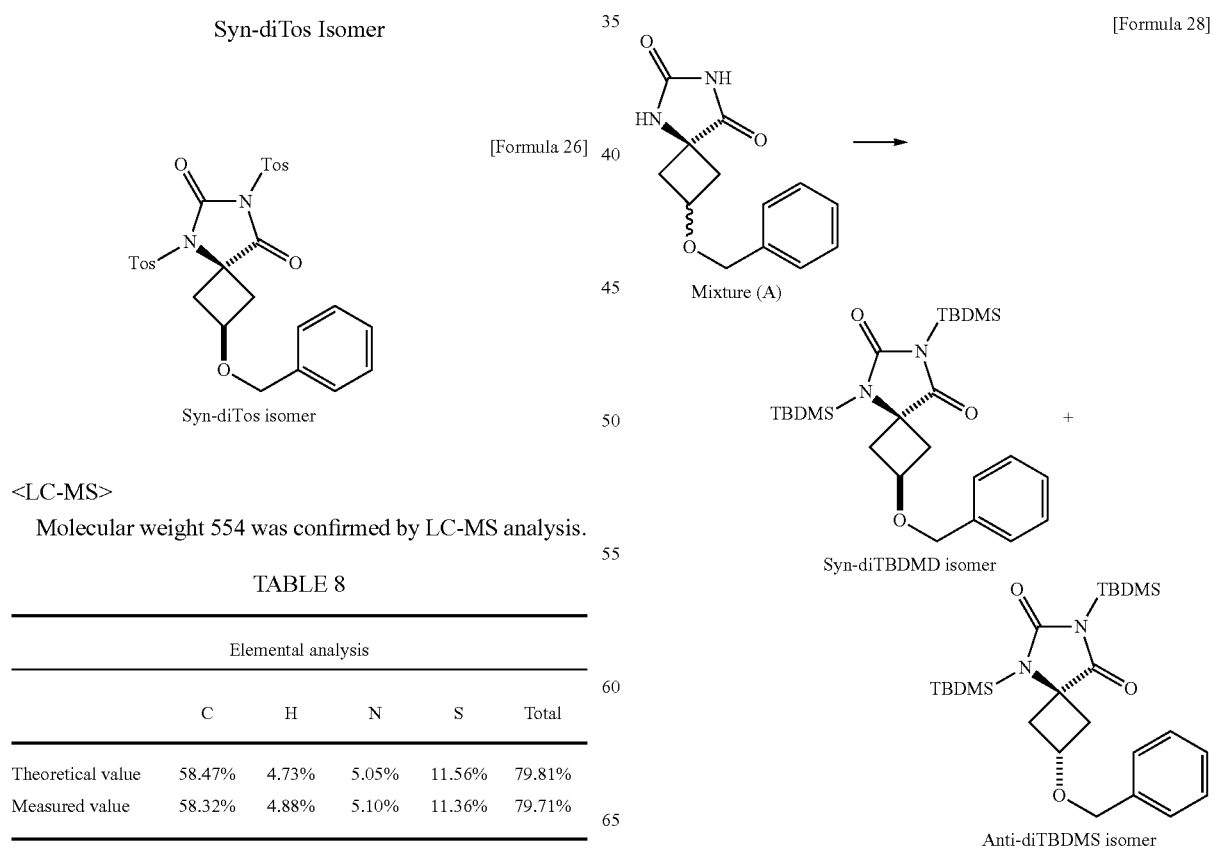

Mixture (A)

Syn-diTBDMD isomer

Anti-diTBDMS isomer

[Formula 28]

An operation was conducted according to that of Example 17 except that tert-butyldimethylsilyl chloride was used in place of the tert-butyloxycarbonyl fluoride used in Example 17.

The oily matter obtained was separated into two components by silica gel chromatography to obtain respective components. LS-MS analysis and elemental analysis confirmed that the two components obtained were (Z)-2-benzyloxy-6,8-dioxo-5,7-diazaspiro[3,4]octan-yl-5,7-di-p-methylphenylsulfone (syn-diTos isomer) and (E)-2-benzyloxy-6,8-dioxo-5,7-diazaspiro[3,4]octan-yl-5,7-di-p-methylphenylsulfone (anti-diTos isomer). The yield of (Z)-2-benzyloxy-6,8-dioxo-5,7-diazaspiro[3,4]octan-yl-5,7-di-p-methylphenylsulfone (syn-diTos isomer) was 10.9 g (yield 58%) and the yield of (E)-2-benzyloxy-6,8-dioxo-5,7-diazaspiro[3,4]octan-yl-5,7-di-p-methylphenylsulfone (anti-diTos isomer) was 2.4 g (13%). There was no other impurity in each component. The result of LC-MS is shown below and the result of elemental analysis is shown in Tables 8 and 9.

Syn-diTos Isomer

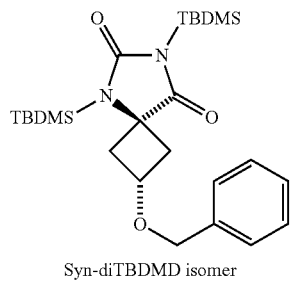

[Formula 29]

Syn-diTBDMD isomer

<LC-MS>

Molecular weight 474 was confirmed by LC-MS analysis.

TABLE 10

| Elemental analysis | | | | | |
|---|---|---|---|---|---|
| | C | H | N | Si | Total |
| Theoretical value | 63.24% | 8.92% | 5.90% | 11.83% | 89.89% |
| Measured value | 63.29% | 8.97% | 5.91% | 11.78% | 89.95% |

Anti-diTBDMS Isomer

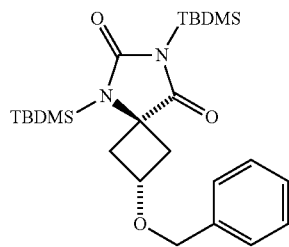

[Formula 30]

Anti-diTBDMS isomer

<LC-MS>

Molecular weight 474 was confirmed by LC-MS analysis.

TABLE 11

| Elemental analysis | | | | | |
|---|---|---|---|---|---|
| | C | H | N | Si | Total |
| Theoretical value | 63.24% | 8.92% | 5.90% | 11.83% | 89.89% |
| Measured value | 63.34% | 9.02% | 6.00% | 11.68% | 89.94% |

Comparative Example 1

1 g of the mixture (A) obtained in Reference Example 1 was purified by silica gel column chromatography. As a result, there was obtained 0.5 g (yield: 50%) of (Z)-2-benzyloxy-5,7-diazaspiro[3,4]octane-6,8-dione (syn-isomer). The content of the anti-isomer was 2%.

The silica gel column used was obtained by filling, in a glass column of 10 mm in inner diameter, 100 g of 45~75 mesh silica gel (Wako Gel C-300, produced by Wako Pure Chemical Industries, Ltd.). The eluent used was 5 liters of methanol/aminoform=2/9 (v/v).

The invention claimed is:

1. A hydantoin ring compound represented by the following formula (II):

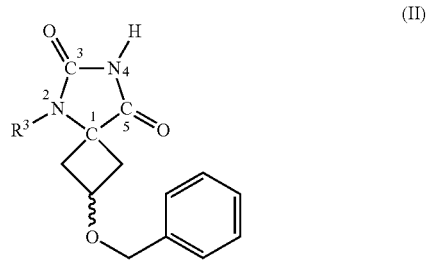

(II)

wherein the numerals attached to individual ring-constituting elements represent the positions of the ring-constituting elements; and $R^3$ is a protective group selected from the group consisting of tert-butyloxycarbonyl group, benzyloxycarbonyl group, tert-butyldimethylsilyl group and tosyl group.

2. A hydantoin ring compound represented by the following formula (III):

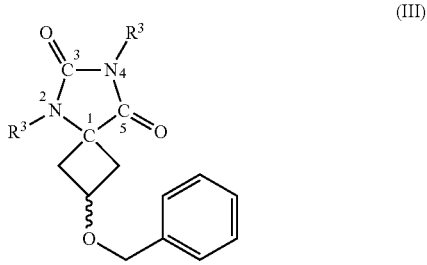

(III)

wherein the numerals attached to individual ring-constituting elements represent the positions of the ring-constituting elements; and $R^3$ is a protective group selected from the group consisting of tert-butyloxycarbonyl group, benzyloxycarbonyl group, tert-butyldimethylsilyl group and tosyl group, wherein two $R^3$s may be different from each other.

* * * * *